US009248256B2

(12) United States Patent
Takagi et al.

(10) Patent No.: US 9,248,256 B2
(45) Date of Patent: Feb. 2, 2016

(54) DEVICE FOR MEDICAL TREATMENT

(71) Applicant: TERUMO KABUSHIKI KAISHA, Shibuya-ku (JP)

(72) Inventors: Toshiaki Takagi, Ashigarakami-gun (JP); Yousuke Ootani, Ashigarakami-gun (JP); Yusuke Sekine, Ashigarakami-gun (JP); Ryuusuke Takashige, Ashigarakami-gun (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 221 days.

(21) Appl. No.: 13/778,579

(22) Filed: Feb. 27, 2013

(65) Prior Publication Data
US 2013/0178828 A1 Jul. 11, 2013

Related U.S. Application Data

(63) Continuation of application No. PCT/JP2011/068520, filed on Aug. 15, 2011.

(30) Foreign Application Priority Data

Aug. 31, 2010 (JP) .................................. 2010-193199

(51) Int. Cl.
A61M 25/00 (2006.01)
A61M 25/01 (2006.01)
A61M 25/10 (2013.01)

(52) U.S. Cl.
CPC ....... A61M 25/0155 (2013.01); A61M 25/0084 (2013.01); A61M 25/1011 (2013.01);
(Continued)

(58) Field of Classification Search
CPC ............ A61M 25/0084; A61M 25/10; A61M 2025/0096; A61M 2025/009; A61M 2025/1052
See application file for complete search history.

(56) References Cited

U.S. PATENT DOCUMENTS 5,464,395 A * 11/1995 Faxon et al. ............. 604/103.02
5,499,630 A * 3/1996 Hiki et al. ..................... 600/461
(Continued)

FOREIGN PATENT DOCUMENTS

JP 5-507230 A 10/1993
JP 2000-232981 A 8/2000
(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA 237) dated Mar. 21, 2013, issued in corresponding International Application No. PCT/JP2011/068520. (5 pages).

(Continued)

Primary Examiner — Scott Medway
(74) Attorney, Agent, or Firm — Buchanan Ingersoll & Rooney PC

(57) ABSTRACT

A medical treatment device enables an injection needle to accurately puncture brain tissue at a prescribed position and a drug solution to be injected into brain tissue, while avoiding damage to the brain tissue as the injection needle is handled. The use of the medical treatment device involves inflating a first balloon located on the outside of a catheter, directing a distal portion of a puncture needle, which is located inside the catheter, to outside the catheter through an opening in the catheter, after which the first balloon is deflated and a second balloon is inflated, and moving the catheter towards the brain tissue located on the opening side so that the injection needle projecting from the opening punctures the brain region.

17 Claims, 5 Drawing Sheets

(52) U.S. Cl.
CPC ...... *A61M25/003* (2013.01); *A61M 2025/0036* (2013.01); *A61M 2025/0092* (2013.01); *A61M 2025/1047* (2013.01); *A61M 2210/0693* (2013.01)

(56) References Cited

U.S. PATENT DOCUMENTS

| | | | |
|---|---|---|---|
| 6,217,554 B1 * | 4/2001 | Green | 604/164.01 |
| 6,283,947 B1 * | 9/2001 | Mirzaee | 604/264 |
| 6,692,466 B1 * | 2/2004 | Chow et al. | 604/164.01 |
| 6,926,692 B2 * | 8/2005 | Katoh et al. | 604/164.01 |
| 7,377,910 B2 * | 5/2008 | Katoh et al. | 604/164.13 |
| 7,850,644 B2 * | 12/2010 | Gonzalez et al. | 604/96.01 |
| 2002/0072706 A1 * | 6/2002 | Hiblar et al. | 604/101.01 |
| 2003/0040712 A1 * | 2/2003 | Ray et al. | 604/173 |
| 2003/0171714 A1 | 9/2003 | Katoh et al. | |

FOREIGN PATENT DOCUMENTS

| | | |
|---|---|---|
| JP | 2001-299927 A | 10/2001 |
| JP | 2003-250899 A | 9/2003 |
| WO | WO 92/10142 A1 | 6/1992 |

OTHER PUBLICATIONS

International Search Report (PCT/ISA/210) issued on Nov. 15, 2011, by the Japanese Patent Office as the International Searching Authority for International Application No. PCT/JP2011/068520.

* cited by examiner

DEVICE FOR MEDICAL TREATMENT

This application is a continuation of International Application No. PCT/JP2011/068520 filed on Aug. 15, 2011, which claims priority to Japanese Patent Application JP2010-193199 filed in Aug. 31, 2010, the entire content of both of which is incorporated herein by reference.

TECHNICAL FIELD

The present invention generally relates to a device for medical treatment. More particularly, the invention pertains to a device for medical treatment that includes an injection needle (infusion needle) in a catheter, with the injection needle being configured to puncture brain tissue for injecting a therapeutic substance such as drug solutions, neurotrophic factors, signal transduction substances, gene, cells, etc.

BACKGROUND DISCUSSION

Known devices for applying medical treatment to a local part in a living body include instruments for medical treatment in which an injection needle is disposed in a catheter so as to be forwardly and rearwardly movable, with the catheter being inserted into the local part or into the vicinity of the local part, and a drug solution is injected via a distal portion of the injection needle into the local part.

As an example, Japanese Application Publication No. 2001-299927 discloses a drug solution injection catheter in which an injection needle projects through a circumferential wall of a catheter inserted in a blood vessel so as to inject a drug solution. In using this catheter, the catheter is first inserted into the inside of the blood vessel, and an expandable-and-contractible balloon section disposed at a distal portion of a shaft section of an elongated flexible tube body is inflated to make close contact with the blood vessel wall, thereby setting and holding the shaft section in a fixed state. Thereafter, the injection needle is projected via a needle hole of the catheter to allow puncture of a cardiac muscle layer at a lesion to inject a predetermined drug solution and thereby perform medical treatment.

The catheter described above exhibits the following difficulty. In a fixed setting state wherein the balloon section is inflated within a blood vessel, an attempt to make the injection needle puncture a desired part may result in the injection needle moving in a playing manner due to the load of a puncture reaction force generated in this instance, thus leading to an error in the puncturing position. As a result, the response of the injection needle to an operation on the proximal side may be worsened, hampering an accurate drug solution injection.

In particular, in a medical treatment applied to an area of the brain, it is necessary to minimize the damage to the brain tissue as the injection needle is handled. It is desirable for the injection needle to be able to puncture a predetermined part of brain tissue without damaging the brain tissue.

SUMMARY

According to one aspect, a device for medical treatment for use in a brain comprises a catheter configured to be positioned in the brain, with the catheter possessing a center axis and an outer circumferential surface, and having an opening in the outer circumferential surface, an injection needle positioned inside the catheter and positionable in facing relation to the opening, and an injection needle bender positioned in the catheter at a position facing the opening, with the injection needle and the injection needle bender being contactable with one another during use of the device to bend the injection needle toward and through the opening so the injection needle projects outwardly beyond the outer circumferential surface of the catheter. A first expandable-and-contractible member is disposed on the outer circumferential surface of the catheter at a position spaced from the opening along an axial direction of the catheter, wherein the first expandable-and-contractible member is expandable to contact brain tissue on an opening side of the catheter at which the opening is located to space the opening side of the catheter from the brain tissue located on the opening side and thereby provide a space for the injection needle after the injection needle is bent by the injection needled bender. A second expandable-and-contractible member is disposed on the outer circumferential surface of the catheter at a position opposite the opening, with the second expandable-and-contractible member being expandable to contact the brain tissue located on the side opposite the opening side to space the outer circumferential surface of the catheter from the brain tissue located on the side opposite the opening side. The first expandable-and-contractible member is contractable so that the expansion of the second expandable-and-contractible member moves the catheter and the injection needle projecting outwardly beyond the outer circumferential surface of the catheter toward the brain tissue on the opening side so that the injection needle punctures the brain tissue on the opening side.

According to another aspect, a device for medical treatment for use in a brain comprises: a catheter possessing a center axis and an outer circumferential surface, and having an opening formed in the outer circumferential surface; an injection needle positioned inside the catheter and configured to project through the opening; and first and second expandable-and-contractible member disposed on the outer circumferential surface of the catheter. The first expandable-and-contractible member is disposed at a position spaced by a predetermined interval from the opening along an axial direction of the catheter, with the first expandable-and-contractible member being configured, when expanded, to contact brain tissue on an opening side of the catheter at which the opening is formed to produce a gap between the catheter and the brain tissue located on the opening side and thereby provide a space for the injection needle to project out through the opening. The second expandable-and-contractible member is disposed on a side of the catheter opposite the opening across the center axis of the catheter, with the second expandable-and-contractible member being configured, when expanded, to contact the brain tissue located on the side opposite to the opening side to produce a gap between the catheter and the brain tissue located on the side opposite to the opening side. The contraction of the first expandable-and-contractible member and expansion of the second expandable-and-contractible member causes the injection needle which is projecting through the opening to project into the space to puncture the brain tissue located on the opening side.

The second expandable-and-contractible member is preferably so disposed as to cover the outer circumferential surface of the catheter along a circumferential direction. In addition, the first expandable-and-contractible member preferably is composed of a balloon, and the second expandable-and-contractible member preferably is composed of a balloon.

The device for medical treatment may further include: an infusion tubing which extends inside the catheter along the axial direction of the catheter and at a distal portion of which the injection needle is disposed; a connecting part which bendably connects the injection needle to a distal portion of the infusion tubing; and bending means by which the injection needle located inside the catheter so as to face the opening is bent at the connecting part, whereby a distal portion of the injection needle is directed outside of the catheter.

The bending means may be in the form of an expandable-and-contractible member for bending the injection needle, with the expandable-and-contractible member being, in a contracted state, disposed inside the catheter so as to face the opening, with the injection needle therebetween, and the expandable-and-contractible member, when expanded, making contact with the injection needle and pushing the injection needle, whereby the injection needle is bent toward the opening. The expandable-and-contractible member for bending the injection needle preferably is composed of a balloon.

Another aspect involves a method of puncturing brain tissue. The method comprises: moving a catheter toward brain tissue, wherein the catheter possesses an outer circumferential surface and a central axis, and has an opening formed in the outer circumferential surface, with an injection needle positioned inside the catheter. The method additionally includes positioning the catheter so that the opening in the outer circumferential surface of the catheter faces toward a portion of the brain tissue to be punctured by the injection needle, creating a space between the outer circumferential surface of the catheter and the portion of the brain tissue to be punctured by the injection needle, with the portion of the brain tissue to be punctured facing an opening side of the catheter at which the opening is formed, bending the injection needle so that the injection needle passes through the opening, projects outwardly beyond the outer circumferential surface of the catheter and is positioned in the space, and moving the catheter as well as the injection needle which is projecting outwardly beyond the outer circumferential surface of the catheter toward the portion of the brain tissue to be punctured so that the injection needle punctures the portion of the brain tissue.

According to the present invention, by both the expansion of the second expandable-and-contractible member disposed on an outer circumferential surface of the catheter on the opposite side from the opening across the center axis of the catheter permitting projection of the injection needle and the contraction of the first expandable-and-contractible member disposed on an outer circumferential surface of the catheter at a position spaced from the opening by a predetermined interval along the axial direction of the catheter, the injection needle projected via the opening can be let puncture a predetermined part of the brain tissue and a drug solution can be injected.

The medical treatment device and method here enable an injection needle to accurately puncture brain tissue at a predetermined position and a drug solution to be injected into the brain tissue, while restraining damage to the brain tissue as the injection needle is handled.

BRIEF DESCRIPTION OF DRAWINGS

FIGS. 4A-4D are partial longitudinal cross-sectional views of the injection needle and illustrating the structure surrounding the opening in the catheter used in the FIG. 1 embodiment in a region between a cranial bone region and a brain region, wherein FIG. 4A illustrates a state before bending of the injection needle, FIG. 4B illustrates a state in which a first balloon has been inflated, FIG. 4C illustrates a state after bending of the injection needle, and FIG. 4D illustrates a state in which the injection needle has punctured the brain region.

DETAILED DESCRIPTION

Figure 1:
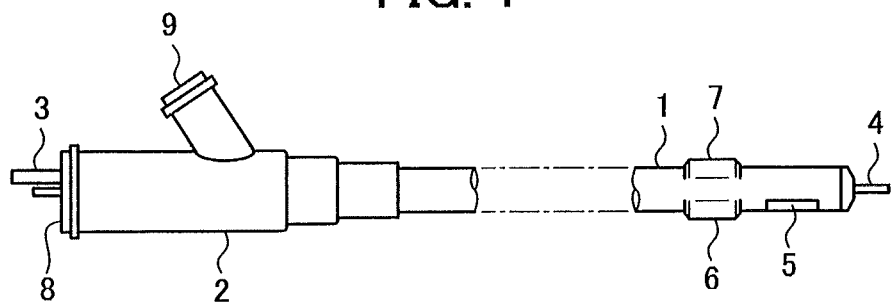
FIG. 1 is a side view of a device for medical treatment according to an embodiment disclosed here.

FIG. 1 shows the external appearance of a device for medical treatment according to one embodiment representing an example of the medical treatment device disclosed here. The device for medical treatment includes a catheter 1, and a branch hub 2 connected to a proximal portion (base end portion) of the catheter 1. The catheter 1 is configured to be inserted into the inside of the brain (for example, the region between the arachnoid and the pia mater (the subarachnoidal cavity)) or into the region between the right brain and the left brain (the longitudinal fissure of cerebrum) during a medical treatment. In the inside of the catheter 1, a drug solution infusion tubing 3 and a guide wire 4 are inserted so as to be forwardly and rearwardly movable. In addition, the catheter 1 is provided with an opening 5 in the outer circumferential surface near a distal portion of the catheter, a first balloon 6 in a deflated state which is disposed on the outer circumferential surface of the catheter 1 at a position spaced proximally from the opening 5 by a predetermined distance along the axial direction of the catheter 1, and a second balloon 7 in a deflated state which is disposed on the outer circumferential surface of the catheter 1 proximal of the opening 5 and on the opposite side from the opening 5 across the center axis of the catheter 1 (i.e., the first and second balloons 6, 7 are positioned at diametrically opposed positions). The first balloon 6 and the second balloon 7 are inflated in a direction (a radial direction of the catheter 1) orthogonal to the axial direction of the catheter 1 by inflow of an expansion fluid (inflation fluid) into the interior of the balloons, and are deflated by outflow of the expansion fluid from the interior of the balloons. The first balloon 6 and the second balloon 7 are examples of a first expandable-and-contractible member and a second expandable-and-contractible member, respectively.

The first balloon 6 is disposed on the side of the outer circumferential surface of the catheter 1 where the opening is formed, preferably at a position near the opening 5. The first balloon 6 may be embedded in the catheter 1, or may be fixed on the outer circumferential surface of the catheter.

The second balloon 7 is disposed at an outer circumferential surface of the catheter 1 on the opposite side across the center axis of the catheter 1 from the outer circumferential surface of the catheter 1 where the opening 5 is formed. The catheter 1 may be embedded in the catheter 1, or may be fixed on the outer circumferential surface of the catheter.

Figure 3:
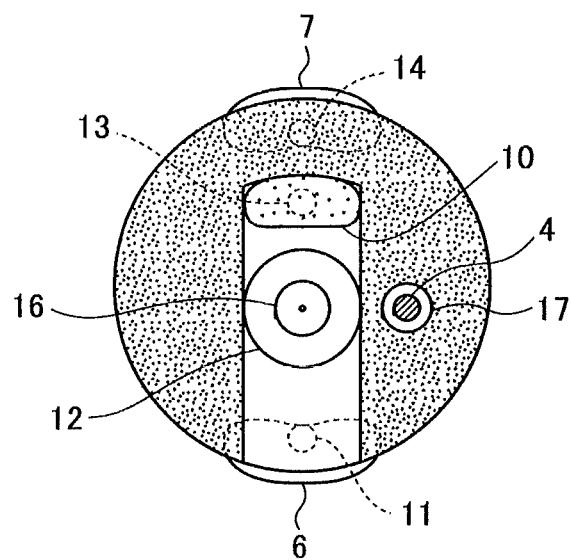
FIG. 3 is an enlarged cross-sectional view taken along the section line III-Ill in FIG. 2.

The positional relationship between the first balloon 6 and the second balloon 7 is not specifically limited. Preferably, as shown in FIG. 3, the first balloon 6 and the second balloon 7 are so disposed as to be opposed to each other, with the center axis of the catheter 1 between the two balloons 6, 7.

The branch hub 2 is provided with: an operating port 8 by which forward and backward movements of the drug solution infusion tubing 3 and the guide wire 4 inserted in the catheter 1 and injection of the drug solution through the drug solution infusion tubing 3 are performed; and a fluid port 9 for performing inflow/outflow of the expansion fluid into and out of the first balloon 6, the second balloon 7, and an injection needle bender in the form of a bending balloon 10 which is disposed inside the catheter 1 as described later.

Figure 2:
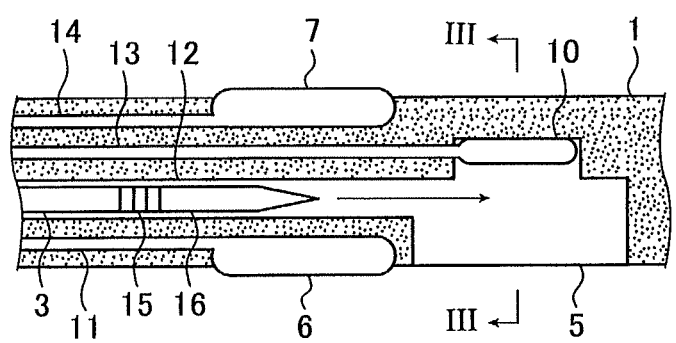
FIG. 2 is a partial longitudinal cross-sectional view of a portion of the medical device shown in FIG. 1 showing the injection needle and the structure surrounding an opening in the catheter.

As shown in FIG. 2, the injection needle bending balloon 10 is disposed inside the catheter 1. The injection needle bending balloon 10 is disposed in the catheter in a deflated state at a position facing the opening 5 and on the inner side of the outer circumferential surface of the catheter 1 on the side opposite to the outer circumferential surface of the catheter 1 where the opening 5 is located. That is, the injection needle bending balloon 10 is positioned in opposing relation to the opening 5. The injection needle bending balloon 10 is inflated and expanded in radial direction of the catheter 1 by inflow of an expansion fluid therein, and is deflated by outflow of the expansion fluid therefrom. The injection needle bending balloon 10 constitutes an expandable-and-contractible member for bending the injection needle in the present invention.

The inside of the catheter 1 is provided with a first lumen 11, a second lumen 12, a third lumen 13, and a fourth lumen 14 which extend in parallel to each other along the axial direction of the catheter 1. The first lumen 11, the third lumen 13, and the fourth lumen 14 are configured to permit the flow of expansion fluids for driving (inflating) the first balloon 6, the injection needle bending balloon 10, and the second balloon 7, respectively. Proximal portions of the first lumen 11, the third lumen 13, and the fourth lumen 14 communicate with the fluid port 9, and distal portions of the first lumen 11, the third lumen 13, and the fourth lumen 14 communicate with the first balloon 6, the injection needle bending balloon 10, and the second balloon 7, respectively. The second lumen 12 is configured to receive the drug solution infusion tubing 3 in a manner allowing the drug solution infusion tubing 3 to be forwardly and rearwardly movable. The proximal portion of the second lumen 12 communicates with the operating port 8, and the distal portion of the second lumen 12 communicates with the opening 5.

An injection needle 16 is connected (in a communicating manner) to a distal portion of the drug solution infusion tubing 3 that is positioned in the second lumen 12. The injection needle 16 is connected to a distal portion of the drug solution infusion tubing 3 through a connecting part 15. The connecting part 15 has a bellows structure configured to permit the injection needle 16 to be relatively easily bent with respect to the drug solution infusion tubing 3.

Furthermore, as shown in FIG. 3, the catheter 1 is provided with an interiorly located fifth lumen 17 extending along the axial direction of the catheter 1 from the operating port 8 to a distal portion of the catheter 1. The guide wire 4 is positioned in the fifth lumen 17 in a manner allowing the guide wire 4 to be forward and backward.

The material forming the catheter 1 is preferably a material which has a certain degree of flexibility. Examples of the material which can be used include thermoplastic resins such as polyolefins such as polyethylene, polypropylene, ethylene-propylene copolymer, ethylene-vinyl acetate copolymer, etc., polyvinyl chloride, polyurethane, polyamides, polyamide elastomers, and polyester elastomers.

In addition, the material(s) forming the first balloon 6 and the second balloon 7 is not particularly limited. However, the first balloon 6 and the second balloon 7 preferably have a multi-layer structure including a base material layer formed of a high-strength polymer (base material layer-forming resin) and a coating layer which is formed on at least a surface of the base material layer and which is formed of a flexible polymer (coating layer-forming resin) more flexible than the high-strength polymer (base material layer-forming resin). Though a variety of configurations are possible, a preferable structure is one in which an inner layer is the base material layer and an outer layer is the coating layer.

The base material layer is formed from a high-strength polymer (base material layer-forming resin). The high-strength polymer (base material layer-forming resin) used to form the base material layer is preferably a stretchable resin. Examples of the material which can thus be used to form the base material layer include polyethylene terephthalate, polyesters (polyethylene terephthalates) obtained by changing a main acid component or a main glycol component of polyethylene terephthalate, mixtures of the above-mentioned polymers, polyamides (nylon 12, nylon 11, MXD6 nylon), and polyarylene sulfides such as PPS (polyphenylene sulfide).

The material of the coating layer is preferably a flexible polymer (coating layer-forming resin) which is in the same series as the high-strength polymer (base material layer-forming resin) used for the base material layer, and is more preferably thermoplastic and stretchable. When polymers in the same series are used to form the base material layer and the coating layer, thermal adhesion or adhesion between both the layers is enhanced. However, a pair of materials enhanced in thermal adhesion or adhesion therebetween by denaturing (modifying) the flexible polymer (coating layer-forming resin) may be used. A pair of materials which are not in the same series but which are capable of thermal adhesion or adhesion to each other may also be used. Furthermore, an adhesive layer may be provided between the base material layer and the coating layer; in this case, the materials may not necessarily be in the same series.

Examples of the flexible polymer (high-polymeric elastomer) which can be used to form the coating layer include polyester elastomers (for example, those polyester elastomers in which the hard segment is composed of an aromatic polyester and the soft segment is composed of an aliphatic polyether, and those polyester elastomers in which the hard segment is composed of an aromatic polyester and the soft segment is composed of an aliphatic polyester), and polyamide elastomers [for example, those polyamide elastomers in which the hard segment is composed of a polyamide (e.g., nylon 12) and the soft segment is composed of a plasticizer, a polyether or a polyester].

The injection needle bending balloon 10 is preferably formed from a high-strength polymer which is stretchable. Examples of the material which can be used to form the injection needle bending balloon 10 include polyethylene terephthalate, polyesters (polyethylene terephthalates) obtained by changing a main acid component or a main glycol component of polyethylene terephthalate, mixtures of these polymers, polyamides (nylon 12, nylon 11, MXD6 nylon), and polyarylene sulfides such as PPS (polyphenylene sulfide).

Now, the manner of operation or method of using the medical device shown in FIGS. 1-3 will be described.

(Catheter Insertion)

Figure 4A:
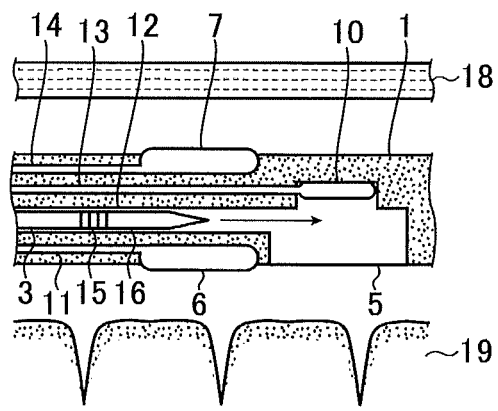

First, as shown in FIG. 1, the guide wire 4 inserted through the operating port 8 into the fifth lumen 17 is projected forward via a distal portion of the catheter 1. Then, with the guide wire 4 as a preceding guide, the distal portion of the catheter 1 is inserted into or moved to a local part needing medical treatment in a brain region or into the vicinity of the local part. In FIG. 4A, the catheter 1 is disposed in the subarachnoidal cavity between a cranial bone region 18, which represents the cranial bones provided at the surface of a lower portion thereof with the arachnoid and dura as brain tissues, and a brain region 19, which represents the cerebrum (brain tissue) provided with the pia mater at the surface thereof. In FIG. 4A, the arachnoid, the dura, and the pia mater as well as the cerebrospinal fluid filling the subarachnoidal cavity are omitted from the drawing. The reference to brain tissues means the tissues present inside the skull (for example, the dura, the arachnoid, the pia mater, the cerebrum, the mesencephalon, the cerebellum, the diencephalons, the medulla oblongata, the ventricle, etc.).

In addition, at the time of inserting the catheter 1, as shown in FIG. 4A, the catheter 1 is preferably so disposed that the first balloon 6 faces the brain region 19 whereas the second balloon 7 faces the cranial bone region 18.

(Injection Needle Projection)

Figure 4B:
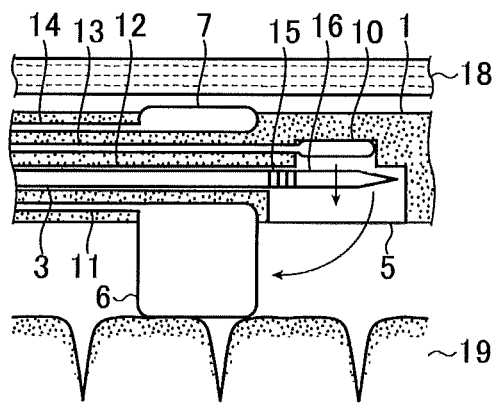

Next, an expansion fluid is introduced into the first balloon 6. That is, an expansion fluid is introduced into the fluid port 9 and flows into the first balloon 6 through the first lumen 11. As a result, inflation of the first balloon 6 is initiated, and the first balloon 6 continues being inflated in directions orthogonal to the axial direction of the catheter 1. When inflated to a predetermined size, the first balloon 6 makes contact with the surface of the brain region 19. When the first balloon 6 continues to be further inflated, a space is produced for permitting the injection needle to project is formed between the brain region 19 and the catheter 1, as shown in FIG. 4B. With such a space (gap) provided, at the time of a bending operation of the injection needle 16 (described later) the injection needle 16 can be projected via the opening 5 to the outside of the catheter 1, without damaging the brain region 19. Preferably, the injection needle 16 can be bent at essentially a right angle with respect to a distal portion of the drug solution infusion tubing 3.

The second balloon 7 may not be in contact with the cranial bone region 18, as shown in FIG. 4B, or may be in contact with the cranial bone region 18. It is preferable for the second balloon 7 to be in contact with the cranial bone region 18, since it is thereby ensured that the catheter 1 can be fixed in a desired position and that the puncturing position of the injection needle 16 can be more securely restrained from deviating from a desired puncturing position.

Subsequently, as shown in FIG. 2, the drug solution infusion tubing 3 inserted in the second lumen 12 of the catheter 1 is moved forward. Then, the forward movement of the drug solution infusion tubing 3 is finished when the injection needle 16, which is disposed via the connecting part 15 on the distal portion of the drug solution infusion tubing 3, reaches a position at which the injection needle 16 faces the opening 5 as shown in FIG. 4B.

Figure 4C:
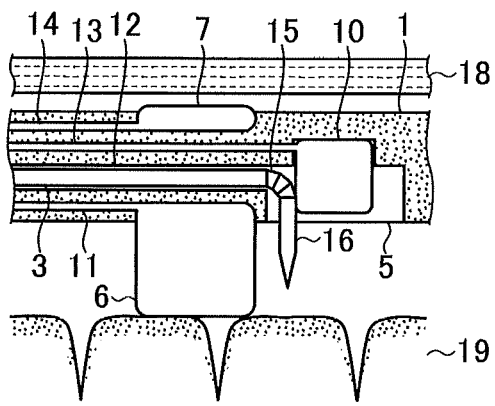

Here, when the expansion fluid is allowed to flow from the fluid port 9 into the injection needle bending balloon 10 through the third lumen 13, inflation of the injection needle bending balloon 10 is started. Then, the injection needle bending balloon 10 contacts the injection needle 16, and continues being inflated while pressing the injection needle 16 toward the opening 5. As a result, the injection needle 16 begins being bent at the connecting part 15 with respect to the distal portion of the drug solution infusion tubing 3. When the injection needle bending balloon 10 is inflated to a predetermined size, as shown in FIG. 4C, the injection needle 16 is bent at essentially a right angle with respect to the distal portion of the drug solution infusion tubing 3. In this case, the drug solution infusion tubing 3 extends in the axial direction of the catheter 1, the injection needle 16 is bent at essentially a right angle with respect to the axial direction of the catheter 1, and a distal portion of the injection needle 16 projects through the opening 5 toward the outside of the catheter 1.

(Injection Needle Puncture)

Next, the first balloon 6 is deflated, and the second balloon 7 is inflated. More specifically, an expansion fluid is permitted to flow from the fluid port 9 into the second balloon 7 through the fourth lumen 14 so that inflation of the second balloon 7 is initiated. Then, the second balloon 7 continues being inflated in directions orthogonal to the axial direction of the catheter 1. When the second balloon 7 is inflated to a predetermined size, it makes contact with the surface of the cranial bone region 18 in the brain. When the second balloon 7 is further inflated, therefore, the gap between the catheter 1 and the cranial bone region 18 is pushed open wider.

On the other hand, at the time of inflation of the second balloon 7, the expansion fluid is drawn out of, or allowed to follow out of, the first balloon 6 via the first lumen 11 and the fluid port 9, whereby the first balloon 6 is deflated.

Figure 4D:
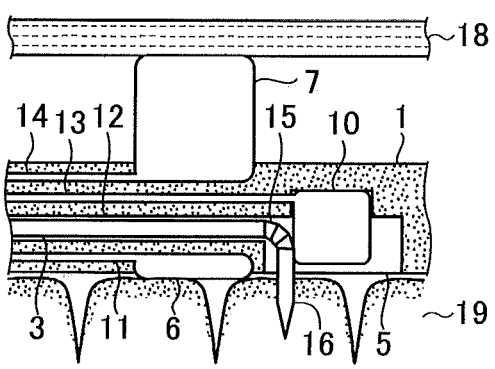

With the first balloon 6 deflated and the second balloon 7 inflated in this manner, the catheter 1 is moved away from the cranial bone region 18; in other words, the catheter 1 is moved toward the brain region 19. As shown in FIG. 4D, the result is that the injection needle 16, in the state of being orthogonal to the axial direction of the catheter 1, punctures the brain region 19 at a desired position, while maintaining that orthogonal state.

After completing a medical treatment, the expansion fluid is allowed to flow through the first lumen 11 into the first balloon 6, whereby the first balloon 6 is inflated. In addition, the expansion fluid is drawn out of the second balloon 7 via the fourth lumen 14 to deflate the second balloon 7, whereby the injection needle 16 can now be pulled out of the brain region 19. After pulling the injection needle 16 out of the brain region 19, the drug solution infusion tubing 3 is moved backward relative to the catheter 1, whereon the injection needle 16 is pulled by the drug solution infusion tubing 3, and is thereby gradually drawn into the second lumen 12 via the connecting part 15. As a result, the injection needle 16 having previously been in the bent state is restored to its original state (straightened state).

As described above, the distal portion of the injection needle 16 projecting outside the catheter 1 punctures a local part of brain tissue and, in this state, a drug solution is supplied through the drug solution infusion tubing 3 into the injection needle 16, whereby the drug solution is injected via the distal portion of the injection needle 16 into the local part of the brain tissue, so as to achieve a medical treatment.

According to the embodiment described above by way of example, the distal portion of the injection needle 16 can project at a right angle with respect to the axial direction of the catheter 1 by inflation of the injection needle bending balloon 10. In addition, the injection needle 16 in the orthogonal state can puncture the brain tissue, while keeping that orthogonal state, by deflating the first balloon 6 and inflating the second balloon 7. Therefore, positioning of the injection needle 16 relative to the local part of the brain tissue is facilitated, and the drug solution can be rather accurately injected into the local part needing administration of the drug solution, while minimizing damage to the brain tissue arising from the puncture with the injection needle 16.

Further, before the injection needle 16 projects outside the catheter 1, the first balloon 6 is inflated, whereby a predetermined space (gap) is formed between the catheter 1 and the brain region 19. This enables a reduction in the risk that the injection needle 16 might make contact with the brain region 19 at the time of being bent. Furthermore, after the medical treatment is finished, the injection needle 16 can be withdrawn from the brain region 19 by moving it in a direction substantially perpendicular to the brain region 19. Accordingly, it is possible to more reliably reduce damage to the brain region 19 at the time of withdrawing the injection needle 16.

Figure 5:
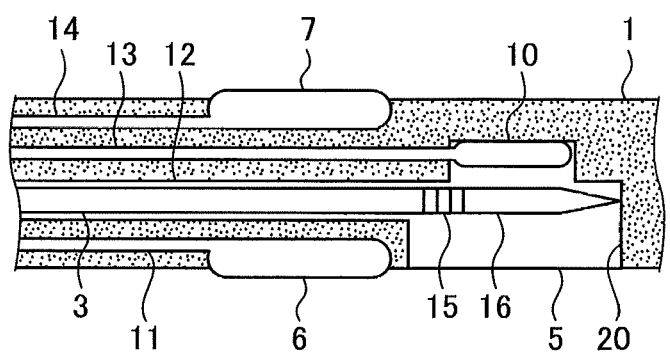
FIG. 5 is a partial longitudinal cross-sectional view of a portion of a medical device according to a modification of the FIG. 1 embodiment showing the injection needle and the structure surrounding an opening in the catheter.

It is possible to detect that the injection needle 16 has reached a position in which the injection needle 16 faces the opening 5 as shown in FIG. 4A during insertion of the drug solution infusion tubing 3 by monitoring the insertion length of the drug solution infusion tubing 3 in relation to the catheter 1. But other detection systems are also possible. For example, an arrangement may be adopted in which the drug solution infusion tubing 3 is inserted into the second lumen 12 of the catheter 1 while monitoring the force applied to the drug solution infusion tubing 3 to move the drug solution infusion tubing 3 in the forward direction, and the contact of the distal portion of the injection needle 16 with a wall part 20 in the catheter 1 corresponding to the position of the opening 5 as shown in FIG. 5 is detected by a change in such force of not less than a predetermined amount. After the contact of the distal portion of the injection needle 16 with the wall part 20 is detected, the drug solution infusion tubing 3 is moved backward by a predetermined distance to separate the distal portion of the injection needle 16 from the wall part 20. In this state, the injection needle bending balloon 10 is inflated so that the injection needle 16 can be bent.

Figure 6A:
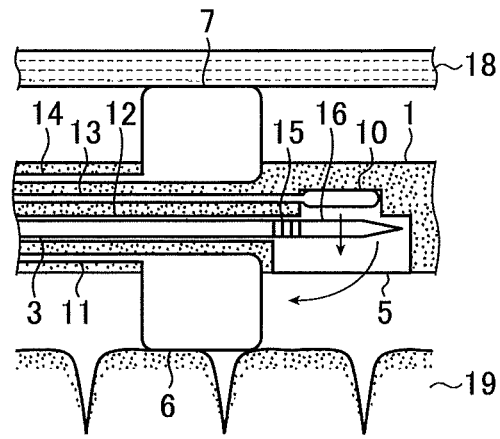
FIGS. 6A-6C are partial longitudinal cross-sectional views illustrating the injection needle and the structure surrounding the opening in the catheter used in Embodiment 1 in a region between a cranial bone region and a brain region, wherein 6A illustrates a state in which a first balloon and a second balloon have been inflated, 6B illustrates a state after bending of the injection needle, and 6C illustrates a state in which the injection needle has punctured the brain region.

As another manner of using or operating the embodiment of the medical treatment device described above, it is possible to perform the injection needle projection aspect of the operation by inflating the first balloon 6 and simultaneously inflating the second balloon 7 such as shown in FIG. 6A.

Specifically, an expansion fluid is permitted to flow from the fluid port 9 into the first balloon 6 via the first lumen 11 and, simultaneously, an expansion fluid is permitted to flow into the second balloon 7 via the fourth lumen 14. When the first balloon 6 and the second balloon 7 are inflated to predetermined sizes (intended extent), the catheter 1 is fixed between the cranial bone region 18 and the brain region 19 through the functions of these balloons. The catheter 1 is thus spaced from the cranial bone region 18 and the brain region 19 by predetermined gaps as shown in FIG. 6A, whereby the catheter 1 is restrained from making contact with the cranial bone region 18 and the brain region 19, so that damage to each of these parts is further reduced.

Figure 6B:
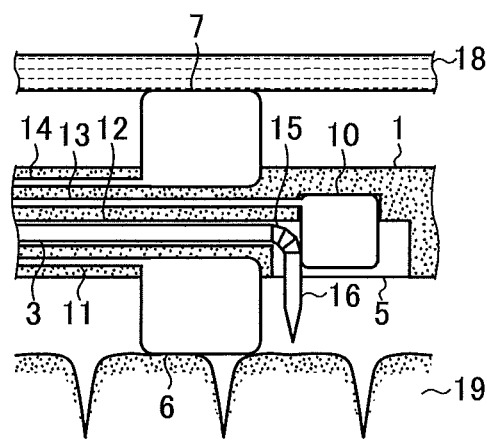

Thereafter, as shown in FIG. 6B, the distal portion of the injection needle 16 can be bent to project outside the catheter 1 via the opening 5 using the same method or operation described above.

Figure 6C:
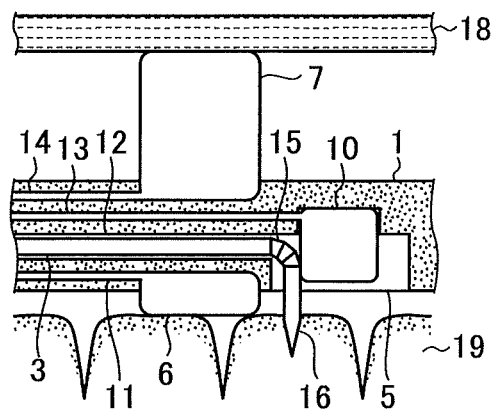

Thereafter, like in the above-discussed injection needle puncture operation, the first balloon 6 is deflated and, simultaneously, the second balloon 7 is inflated (further inflated) so that the injection needle 16 punctures the brain region 19 at a desired position (FIG. 6C).

FIG. 6C illustrates the mode in which the second balloon 7 is further inflated. In this connection, in the case where the first balloon 6 and the second balloon 7 are inflated to large extents in the injection needle projecting step, the pressure from the first balloon 6 causes the brain region 19 to be moved to a position spaced more from the cranial bone region 18, as compared with its position before contact with the first balloon 6. In such a case, by deflating the first balloon 6 while maintaining the inflated state of the second balloon 7 in the puncturing step, it is also possible for the injection needle 16 to puncture the brain region 19 at a desired position by utilizing the action of the brain region 19 to return to its position before the movement.

In the embodiment described above, only one second balloon 7 is provided on the opposite side from the opening 5 and on a straight line interconnecting the opening 5 and the center axis of the catheter 1. An alternative configuration may also be adopted in which two second balloons 7 are provided on the opposite side from the opening 5 and on both sides of the straight line interconnecting the opening 5 and the center axis of the catheter 1.

Similarly, two first balloons 6 may be provided on the side of the opening 5.

Figure 7:
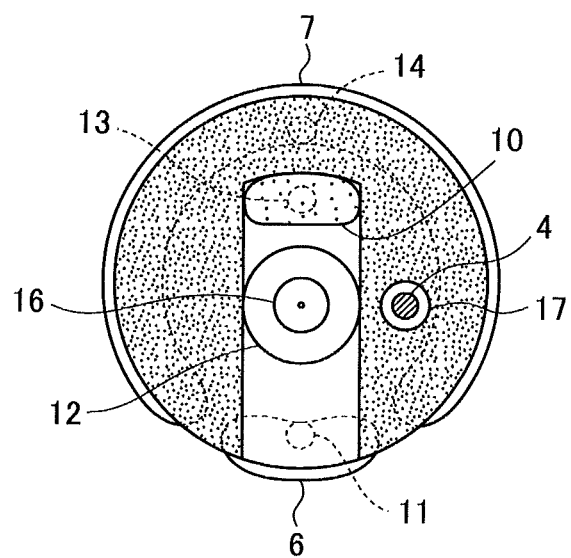
FIG. 7 is an enlarged cross-sectional view of another embodiment of the medical device.

FIG. 7 shows the structure of a major part of a catheter 101 for use in a device for medical treatment according to another embodiment.

The catheter 101 is the same as the catheter 1 described above and shown in FIG. 1, except that the second balloon 7 is disposed to cover the outer circumferential surface of the catheter along the circumferential direction. The second balloon 7 is configured to cover at least one half (preferably 60% to 80%) of the outer circumference (circumferential extent) of the catheter 101, as viewed in the cross-section of the catheter 101.

In this second embodiment, in the case where the catheter 101 is inserted into the brain tissue such as the longitudinal fissure of cerebrum between the right brain and the left brain, it is possible by inflation of the second balloon 7 to push open wider the whole brain tissue surrounding the catheter 101. Consequently, the area of contact between the balloon 7 and the brain tissue is enlarged, so that the contact between the brain tissue and the catheter 101 can be restrained more securely. In addition, the stress exerted on the brain tissue by the catheter 101 can be dispersed, so that damage to the brain tissue can be reliably restrained. The increase in the area of contact between the balloon 7 and the brain tissue makes it easier to stably hold the catheter 101.

The manner of operation or use of this second embodiment of the medical treatment device can be the same as the operational procedure and variations described above.

The first embodiment of the medical treatment device is configured so that the injection needle 16 communicates with the distal portion of the drug solution infusion tubing 3 via the connecting part 15 having the bellows structure. But the medical treatment device is not limited in this regard. For example, a configuration may be adopted in which the injection needle 16 communicates with the distal portion of the drug solution infusion tubing 3 via a connecting part having a hinge structure.

The connecting part 15 having the hinge structure may be provided with a snap mechanism or stopper to stabilize a turning angle in a state where the injection needle 16 is bent at a right angle with respect to the distal portion of the drug solution infusion tubing 3. In such a case, the injection needle 16 can be bent rather accurately at a right angle with respect to the axial direction of the catheter 1.

The manner of using such an embodiment of the medical treatment device can be the same as the operational procedure and variations described above.

While the drug solution infusion tubing 3 is inserted in the catheter 1, 101 so as to be forwardly and backwardly movable within the second lumen 12 in the above-described embodiments, the invention is not limited in this regard. For example, a configuration may be adopted in which the drug solution infusion tubing 3 is fixed in the catheter 1, 101 in the state where the injection needle 16 is located to face the opening 5 as shown in FIG. 4B, insofar as the injection needle 16 can be bent at essentially a right angle with respect to the axial direction of the catheter by inflation of the injection needle bending balloon 10. In this case, a configuration can also be adopted in which, instead of using an independent drug solution infusion tubing 3, the second lumen 12 functions as a drug solution infusion tubing, and the injection needle 16 communicates with a distal portion of the second lumen 12 via the connecting part 15.

Figure 8:
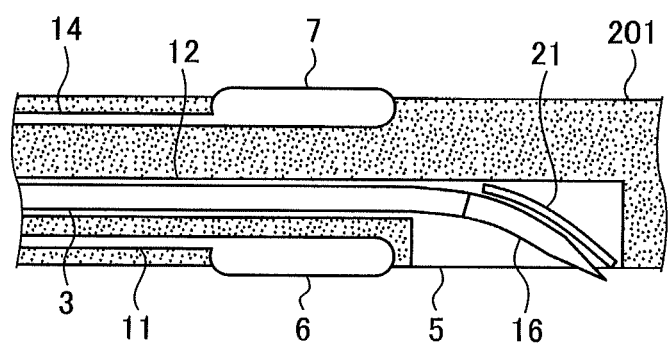
FIG. 8 is a partial longitudinal cross-sectional view of a portion of the medical device according to another embodiment showing the injection needle and the structure surrounding an opening in the catheter.

The above-described embodiments of the medical treatment device are configured so that the injection needle 16 is bent and projects through the opening 5 by an injection needle bender, namely inflation of the injection needle bending balloon 10. The injection needle bending balloon 10 is an example of means for bending the injection needle 16 (at the connecting part) so that the injection needle projects through the opening outwardly of the catheter. The means for projecting the injection needle 16 via the opening 5 is not limited to this configuration. For instance, a different injection needle bender may be adopted in which an injection needle guide section 21 inclined relative to the axial direction of the catheter is adjacently disposed at a position facing the opening 5, as shown in FIG. 8. In this case, as shown in FIG. 8, when the drug solution infusion tubing 3 formed with the injection needle 16 at the distal portion of the drug solution infusion tubing 3 is moved forward within and along the second lumen 12, the injection needle 16 makes contact with the injection needle bender or guide section 21 and is guided (bent) by the inclined surface of the injection needle guide section 21 to project outside the catheter 201 by way of the opening 5.

The shape of the surface of the injection needle guide section 21 with which the injection needle 16 makes contact is not limited to the curved surface shown in FIG. 8, but may be a flat surface or straight surface.

In addition to the operation and effect obtained in the above-described embodiments of the medical treatment device, this embodiment of the medical treatment device simplifies the catheter structure.

The operation, or manner of using, this embodiment of the medical treatment device shown in FIG. 8 will now be described. First, like in the injection needle projection operation described above, the first balloon 6 is inflated and then the injection needle 16 is moved forward to a predetermined position so as to project via the opening of the catheter 201. Thereafter, like in the puncturing operation described above, the injection needle 16 is caused to puncture the brain region 19.

The above-described embodiments of the medical treatment device are configured to allow the injection needle to puncture the brain tissue at a predetermined position by utilizing the pressure generated by inflation of the balloon, after once projecting the injection needle outside of the catheter. Therefore, an error in the puncturing position due to the load of a puncture reaction force is not liable to occur. It is thus possible to attain more excellent safety and operability.

The detailed description above describes features and aspects of embodiments of a medical treatment device disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A device for medical treatment for use in a brain comprising:
a catheter configured to be positioned in the brain, the catheter possessing a center axis and an outer circumferential surface, and having an opening in the outer circumferential surface;
an injection needle positioned inside the catheter, the injection needle being positionable in facing relation to the opening;
an injection needle bender positioned in the catheter at a position facing the opening, the injection needle and the injection needle bender being contactable with one another during use of the device to bend the injection needle toward and through the opening so the injection needle projects outwardly beyond the outer circumferential surface of the catheter;
a first expandable-and-contractible member on the outer circumferential surface of the catheter at a position spaced from the opening along an axial direction of the catheter, the first expandable-and-contractible member being expandable to contact brain tissue on an opening side of the catheter at which the opening is located to space the opening side of the catheter from the brain tissue located on the opening side and thereby provide a space for the injection needle after the injection needle is bent by the injection needled bender; and
wherein the injection needle bender is an expandable and contractible balloon, the balloon being expandable to contact the injection needle and bend the injection needle.

2. A device for medical treatment for use in a brain comprising:
a catheter possessing a center axis and an outer circumferential surface, and having an opening formed in the outer circumferential surface;
an injection needle positioned inside the catheter and configured to project through the opening;
a first expandable-and-contractible member disposed on the outer circumferential surface of the catheter at a position spaced by a predetermined interval from the opening along an axial direction of the catheter, the first expandable-and-contractible member being configured, when expanded, to contact brain tissue on an opening side of the catheter at which the opening is formed to produce a gap between the catheter and the brain tissue located on the opening side and thereby provide a space for the injection needle to project out through the opening;
a second expandable-and-contractible member disposed on the outer circumferential surface of the catheter on a side opposite from the opening across the center axis of the catheter, the second expandable-and-contractible member being configured, when expanded, to contact the brain tissue located on the side opposite to the opening side to produce a gap between the catheter and the brain tissue located on the side opposite to the opening side;
the first expandable-and-contractible member and the second expandable-and-contractible member being configured so that the second expandable-and-contractible member is expanded, while the first expandable-and-contractible member is contracted, to move the catheter and the injection needle toward the brain tissue on the opening side of the catheter so that the injection needle punctures the brain tissue located on the opening side;

infusion tubing extending inside the catheter along the axial direction of the catheter and at a distal portion of the catheter at which the injection needle is disposed;

a connecting part connecting the injection needle to a distal portion of the infusion tubing, the connecting part being configured to permit the injection needle to bend relative to the infusion tubing to allow the needle to project through the opening;

bending means for bending the injection needle located inside the catheter in facing relation to the opening so that a distal portion of the injection needle is directed outside the catheter; and the bending means including a third expandable-and-contractible member disposed inside the catheter in a contracted state in facing relation to the opening, with the injection needle positioned between the third expandable-and-contractible member and the opening, the third expandable-and-contractible member, when expanded, making contact with the injection needle and pushing the injection needle, whereby the injection needle is bent toward the opening.

3. The device for medical treatment according to claim 1, wherein the first expandable-and-contractible member is a balloon.

4. The device for medical treatment according to claim 2, further comprising
an injection needle bender plate positioned to be contacted by the injection needle when the injection needle moves in the forward direction, the plate being configured to cause the injection needle to bend toward the opening and project through the opening and outwardly beyond the outer circumferential surface of the catheter.

5. The device for medical treatment according to claim 2, wherein the second expandable-and-contractible member covers at least one-half the outer circumferential surface of the catheter along a circumferential direction when viewed in transverse cross-section.

6. The device for medical treatment according to claim 2, wherein the first expandable-and-contractible member comprises a balloon.

7. The device for medical treatment according to claim 2, wherein the second expandable-and-contractible member comprises a balloon.

8. The device for medical treatment according to claim 2, wherein the third expandable-and-contractible member for bending the injection needle comprises a balloon.

9. The device for medical treatment according to claim 5, wherein the first expandable-and-contractible member comprises a balloon.

10. The device for medical treatment according to claim 5, wherein the second expandable-and-contractible member comprises a balloon.

11. The device for medical treatment according to claim 6, wherein the second expandable-and-contractible member comprises a balloon.

12. The device for medical treatment according to claim 5, further comprising:
infusion tubing extending inside the catheter along the axial direction of the catheter and at a distal portion of the catheter at which the injection needle is disposed;

a connecting part connecting the injection needle to a distal portion of the infusion tubing, the connecting part being configured to permit the injection needle to bend relative to the infusion tubing to allow the needle to project through the opening; and bending means for bending the injection needle located inside the catheter in facing relation to the opening so that a distal portion of the injection needle is directed outside the catheter.

13. The device for medical treatment according to claim 6, comprising:
infusion tubing extending inside the catheter along the axial direction of the catheter and at a distal portion of the catheter at which the injection needle is disposed;

a connecting part connecting the injection needle to a distal portion of the infusion tubing, the connecting part being configured to permit the injection needle to bend relative to the infusion tubing to allow the needle to project through the opening; and bending means for bending the injection needle located inside the catheter in facing relation to the opening so that a distal portion of the injection needle is directed outside the catheter.

14. The device for medical treatment according to claim 7, comprising:
infusion tubing extending inside the catheter along the axial direction of the catheter and at a distal portion of the catheter at which the injection needle is disposed;

a connecting part connecting the injection needle to a distal portion of the infusion tubing, the connecting part being configured to permit the injection needle to bend relative to the infusion tubing to allow the needle to project through the opening; and bending means for bending the injection needle located inside the catheter in facing relation to the opening so that a distal portion of the injection needle is directed outside the catheter.

15. A method of puncturing brain tissue comprising:
moving a catheter toward brain tissue, the catheter possessing an outer circumferential surface and a central axis, and having an opening formed in the outer circumferential surface, with an injection needle positioned inside the catheter;

positioning the catheter so that the opening in the outer circumferential surface of the catheter faces toward a portion of the brain tissue to be punctured by the injection needle;

creating a space between the outer circumferential surface of the catheter and the portion of the brain tissue to be punctured by the injection needle, the portion of the brain tissue to be punctured facing an opening side of the catheter at which the opening is formed;

bending the injection needle so that the injection needle passes through the opening, projects outwardly beyond the outer circumferential surface of the catheter and is positioned in the space; and moving the catheter as well as the injection needle which is projecting outwardly beyond the outer circumferential surface of the catheter toward the portion of the brain tissue to be punctured so that the injection needle punctures the portion of the brain tissue.

16. The method according to claim 15, wherein the creating of the space between the outer circumferential surface of the catheter and the portion of the brain tissue to be punctured by the injection needle comprises expanding an expandable-and-contractible member disposed on the outer circumferential surface of the catheter to cause the expandable-and-contractible member to contact the brain tissue and urge catheter away from the portion of the brain tissue.

17. The method according to claim 15, wherein the moving of the catheter as well as the injection needle comprises expanding an expandable-and-contractible member disposed on the outer circumferential surface of the catheter to cause the expandable-and-contractible member to contact the brain tissue opposite the portion of the brain tissue.

* * * * *